United States Patent [19]

Vogelhut

[11] 4,231,754

[45] Nov. 4, 1980

[54] CHEMILUMINESCENT ANALYTICAL DEVICE

[75] Inventor: Paul O. Vogelhut, Mishawaka, Ind.

[73] Assignee: Miles Laboratories, Inc., Elkhart, Ind.

[21] Appl. No.: 41,682

[22] Filed: May 23, 1979

[51] Int. Cl.$^3$ .................. G01N 21/76; G01N 33/50
[52] U.S. Cl. .................. 23/230 R; 23/230 B; 422/52; 422/56; 422/57; 435/11; 435/14; 435/25; 435/805
[58] Field of Search .................. 422/52, 56, 57; 23/230 R, 230 B, 232 R; 435/11, 14, 25, 805; 252/408

[56] References Cited

U.S. PATENT DOCUMENTS

| | | | |
|---|---|---|---|
| 3,690,832 | 9/1972 | Plakas | 422/52 X |
| 3,712,793 | 1/1973 | Lyshkow | 422/52 X |
| 3,901,657 | 8/1975 | Lightfoot | 422/56 |
| 3,923,462 | 12/1975 | Cavanagh | 422/52 X |

*Primary Examiner*—R. E. Serwin
*Attorney, Agent, or Firm*—Charles J. Herron

[57] ABSTRACT

A device, method of making the device and method for determining a constituent in a sample by production of luminescence are disclosed. More particularly, there is provided a test device for determining an analyte in a sample comprising unitary solid carrier means incorporated with a first reagent system responsive to the presence of said analyte to produce a reaction product and a second reagent system responsive to the presence of said reaction product to produce luminescence. The test device can further comprise a photoresponsive layer physically associated with said carrier means and responsive to light produced by the chemiluminescent system.

12 Claims, No Drawings

CHEMILUMINESCENT ANALYTICAL DEVICE

FIELD OF THE INVENTION

The present invention relates generally to the field of reagent tests and, more particularly, to a chemiluminescent analytical device and method for detecting a constituent in a sample using said device.

BACKGROUND OF THE INVENTION

The prior art has developed a wide variety of test means for the determination of specific constituents in liquids such as urine and blood. These have taken a variety of forms, one of the most popular being reagent impregnated test strips of the dip-and-read type, certain of which are useful for the determination of such constituents as glucose, protein, occult blood, and the like in body fluids, whereas others are useful for the determination of various constituents in other liquids, such as swimming pool water, cutting fluid, and the like.

Such prior art test systems have conventionally been of the type which include in the reagent composition one or more chromogenic redox indicators which are either directly responsive to the analyte to be determined or are combined with and react to the product of an analyte responsive system. Recently, methods have been developed whereby chemiluminescent techniques have been used for determination of glucose in blood [Bostik D. T. et al. Anal. Chem., 47:447–452 (1975)] and in urine [Williams, D. C. et al. Clin. Chem., 22:372–374 (1976)]. These determinations have made use of glucose oxidase immobilized to a column through which a test sample is passed by positive pressure using an infusion pump and syringe. As the glucose sample enters the column, hydrogen peroxide is generated and carried out of the column with the column effluent to an optically clear cell in which it reacts with luminol ferricyanide in a liquid system. The chemiluminescence produced is detected by a separate photomultiplier tube which is attached to the face of the cell. The signal is then amplified by various photometric preamplifiers and recorded by a potentiometric recorder.

More recently an automated chemiluminescent method for detemining nicotinamide adenine dinucleotide, such as is used in lactate dehydrogenase determinations, was published by Williams, D. C. et al, Anal. Chem., 48: 1478–1481 (1976). A segmented flow system driven by a peristaltic pump was used.

Another apparatus which has been suggested for chemiluminescent determination is simply prepared by injecting a sample and chemiluminescent reagents into a sealed container surrounded by photographic film and measuring the film exposure as a function of concentration. [Seitz, W. R. et al. Anal. Chem., 46:188–202, at 191–192 (1974)].

Coffman, U.S. Pat. No. 3,239,406 discloses a chemiluminescent tape useful as a marker. Upon exposure to air the tape chemiluminesces for different periods of time and at different levels of illumination depending upon the type and amount of chemiluminescent composition incorporated in the structure. The tape comprises at least one layer or surface which is adhesive to other surfaces and which has at least a surface impregnated with a chemiluminescent composition containing at least one peraminoethylene and a strippable film overcoat or removable envelope to protect the peraminoethylene composition from exposure to oxygen prior to use.

Cavanagh, U.S. Pat. No. 3,923,462, discloses an automated apparatus for the detection of ozone in ambient air. A sample of air is passed through a light tight enclosure where it reacts with a material such as Rhodamine B, which luminesces in the presence of ozone, or a material which normally luminesces (such as in black light) and is quenched in the presence of ozone. Photographic film is positioned in the enclosure and spaced apart from the chemiluminescent system. The film is in exposed relationship to the luminescent reaction inside of the light tight enclosure. The pressure, such as atmospheric pressure, of the substance to be detected must be determined independently of film density, thus requiring two separate measurements and use of sophisticated and expensive equipment.

Thus, it can be seen that the application of chemiluminescence has been as markers, indicators of gas content and, in expensive continuous flow column techniques, luminescent reactions have been used in analytical chemistry. Despite the development of the dip-and-read test device industry and the attempts at application of luminescence reactions to analytical chemistry it is evident that methodologies to which each are applicable have been limited in scope. Substantial areas of analysis have not heretofore been possible with conventional dip-and-read test devices because of the detection ranges to which chromogenic indicators are limited. Likewise the areas of analysis to which prior art luminescent systems have been applicable is limited by the size, expense, complexity and susceptibility to interference which are characteristic of the methods disclosed.

OBJECTS OF THE INVENTION

It is a principal object of the present invention to provide a test device for determining an analyte in a sample using a unitary solid carrier means incorporated with a first reagent system responsive to the presence of said analyte to produce a reaction product and a second reagent system responsive to the presence of said reaction product to produce luminescence.

It is another object to provide a test device which further comprises a photoresponsive layer physically associated with said carrier means and responsive to the light produced by the chemiluminescent system.

It is yet another object to provide a test device having first and second matrix layer in laminate relation and a gas permeable, liquid impermeable intermediate layer, interposed therebetween, whereby gas can pass to and from one matrix layer to cause a response in the other matrix layer without passage of interfering substances.

It is yet another object to provide a process for preparing the disclosed test device.

An additional object of the invention is to provide a convenient, inexpensive test device for quantitative analytical examination of extremely small quantities of analyte using a chemiluminescent system.

A further object is to provide a rapid and convenient method for determining an analyte in a sample using the disclosed test device.

Other objects and a fuller understanding of the invention will be had by referring to the following description and claims drawn to preferred embodiments thereof.

SUMMARY OF THE INVENTION

In accordance with the present invention there is provided a device, method of making the device and method for determining a constituent in a sample by production of luminescence. More particularly, there is provided a test device for determining an analyte in a sample comprising unitary solid carrier means incorporated with a first reagent system responsive to the presence of said analyte to produce a reaction product and a second reagent system responsive to the presence of said reaction product to produce luminescence. The test device can further comprise a photoresponsive layer physically associated with said carrier means and responsive to light produced by the chemiluminescent system.

DESCRIPTION OF THE PREFERRED EMBODIMENTS

Although specific terms are used in the following description for the sake of clarity, these terms are intended to refer only to the particular embodiments of the invention selected for exemplary illustration, and are not intended to define or limit the scope of the invention.

In one preferred embodiment, the chemiluminescent test device is such that the carrier means comprises at least one layer having the first reagent system incorporated therewith and at least one other layer having the second reagent system incorporated therewith, the layers incorporating said first and second systems having surface portions in contact. Alternately, the test device can have a separation layer present between the layers incorporating the first and second reagent system, in which the separation layer permits passage of the reaction product of the reagent system therethrough. This separation layer can be a gas permeable and liquid impermeable intermediate layer. The separation of layers can also be such that a pH gradient is formed between the reagent layer and the chemiluminescent layer.

In another preferred embodiment, the test device further comprises a photoresponsive layer physically associated with the carrier means and responsive to light produced by the chemiluminescent system. In this embodiment the reagent system can be incorporated with a first layer and the chemiluminescent system incorporated with a second layer of said carrier, the first layer having at least one surface in contact with the second layer so as to permit passage of the reaction product from the first layer to the second layer, and wherein the photoresponsive layer physically contacts at least one surface of said second layer other than that surface of the second layer which is in contact with the first layer. The photoresponsive layer can be removable from the carrier means and can optionally have means for protecting said photoresponsive layer from ambient light, such as an opaque protective layer covering that surface not in contact with the second layer.

The test device can be such that the chemiluminescent system is encapsulated so as to be releasable by contact with the sample and effective after such release to react with the reaction product of the reagent system. Microcapsules are preferably used for encapsulation and can be formed by any conventional microencapsulation techniques so as to contain the necessary reagents for the chemiluminescent system. For example, see Greyson, U.S. Pat. No. 4,015,462 and Adams, U.S. Pat. No. 3,092,463. The microcapsules are preferably osmosensitive; release of their contents being effected thereby. They can also be formed of material soluble in the sample solution.

The expression "carrier means" refers to matrices which are insoluble in and maintain their structural integrity when exposed to physiological or other liquid. Suitable matrices which can be used include paper, cellulose, wood, synthetic resin fleeces, glass fiber, nonwoven and woven fabrics, gelatin, various organic polymers, such as polypropylene, and other organic materials well known as film formers to those skilled in the art. For convenience the carrier means can be associated with an insoluble support member, such as can be made of polystryene.

In any of the embodiments of the test device described above the reagent system is preferably of the type which comprises at least one enzyme responsive to the presence of the analyte in the sample to produce a reaction product, such as an oxidant. This enzyme is characteristically an oxidase, such as those known to be used in clinical analysis, such as glucose oxidase or cholesterol oxidase. The oxidant formed is a peroxidatively active substance such as hydrogen peroxide. Other known oxidants which are formed or used in other systems include periodate, ferricyanide or permanganate.

Likewise, in any embodiment of the test device disclosed the system responsive to the presence of the reaction product to produce luminescence can include a compound having the formula:

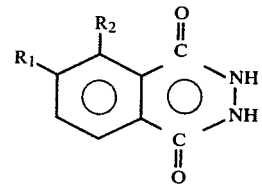

wherein one of $R_1$ and $R_2$ is hydrogen and the other is $-NR_3R_4$ wherein $R_3$ and $R_4$ are independently selected from hydrogen or a straight chain alkyl group containing 1–6 carbon atoms. The preferred compound is luminol (5-amino-2,3-dihydro-1,4-phthalazinedione).

Other compounds known for their ability to produce luminescence in response to oxidation include tetrabis-(dimethylamino) ethylene, luciferin (of bacterial or firefly origin), lucigenin (dimethyl diacridinum nitrate) and oxalyl chloride.

The chemiluminescent system is preferably one which comprises at least one chemiluminescent compound and a catalyst which can comprise a ferric (F+++) ion, hemoglobin, hematin, or products derived from microperoxidase. Other catalysts useful in combination with chemiluminescent compounds are disclosed in the references referred to as constituting the background for this invention.

The oxidant-responsive chemiluminescent system can further comprise a buffer effective to provide a pH of from about 8.5 to about 12.5. Use of a barbitol buffer is preferred and results in a pH of about 8.5.

When the test device is such as to further include a photoresponsive layer, such layer is preferably a photoresponsive imaging layer of the type which is permanently transformed by exposure to a light response produced by the oxidant-responsive chemiluminescent system. Such photoresponsive imaging layers can be of the type which are permanently transformed by exposure to a light response in proportion to the amount of light emitted. These include photographic film, particularly self-developing photographic black and white film and color film.

Further included in the invention is a method for determination of a constituent in the sample which comprises contacting the sample with the devices described above and observing any detectable chemiluminescent response. Where a photoresponsive layer is incorporated with the device the method for determination comprises contacting the sample with the device and observing any detectable exposure of the photoresponsive layer.

The device can be prepared by a method which comprises incorporating a carrier with a reagent system responsive to the presence of an analyte to produce an oxidant and an oxidant-responsive chemiluminescent system in fluid contact with the reagent system. In a multilayered device the method comprises incorporating at least one layer of the carrier means with a reagent system responsive to the presence of an analyte to produce an oxidant and incorporating at least one other layer of the carrier with an oxidant-responsive chemiluminescent system in fluid contact with the reagent system. Where the device is intended to have a photoresponsive layer associated with it the method for preparing the device comprises incorporating a carrier with a reagent system responsive to the presence of an analyte to produce an oxidant and an oxidant-responsive chemiluminescent system in fluid contact with the reagent system, and physically associating a responsive layer with the carrier so as to be in light contact with the chemiluminescent system.

Although the invention has been described with a certain degree of particularity, it is understood that the present disclosure has been made only by way of example and that numerous changes in the details can be resorted to without departing from the scope of the invention.

What is claimed is:

1. A test device for determining an analyte in a sample comprising at least one layer incorporated with a first reagent system responsive to the presence of said analyte to produce a reaction product and at least one luminescent layer having a second reagent system responsive to the presence of said reaction product to produce luminescence, and in which there is a pH gradient between the first reagent system layer and the luminescent layer.

2. The test device of claim 1 wherein a separation layer is present between the layers incorporating said first and second reagent systems, which separation layer permits passage of the reaction product therethrough.

3. The test device of claim 2 which further comprises a photoresponsive layer physically associated with said test device and responsive to light produced by the second reagent system which is a luminescent system.

4. The test device of claim 1 wherein the first reagent system is incorporated with a first layer and the luminescent reagent system is incorporated with a second layer, the first layer having at least one surface in contact with the second layer so as to permit passage of the reaction product from the first layer to the second layer, and which further comprises a photoresponsive layer in contact with at least one surface of said second layer which is in contact with the first layer.

5. The test device of claim 4 wherein the photoresponsive layer is a photoresponsive imaging layer of the type which is permanently transformed by exposure to a light response in proportion to the amount of light emitted.

6. A method for determination of a constituent in a sample which comprises contacting the sample with the device of claim 4 and observing any detectable exposure of the photoresponsive layer.

7. A method for preparing the test device of claim 4 which comprises incorporating at least one layer with a first reagent system responsive to the presence of an analyte to produce a reaction product and at least one other layer with a second reagent system responsive to the presence of the reaction product to produce luminescence and physically associating a photoresponsive layer with the test device so as to be in light contact with the second reagent system.

8. The test device of claim 1 wherein said first reagent system comprises at least one enzyme responsive to the presence of the analyte in the sample to produce an oxidant.

9. The test device of claim 1 wherein the second reagent system includes a compound having the formula:

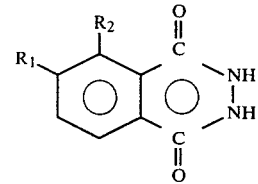

wherein one of $R_1$ and $R_2$ is hydrogen and the other is $-NR_3R_4$ wherein $R_3$ and $R_4$ are independently selected from hydrogen or a straight chain alkyl group containing 1-6 carbon atoms.

10. The test device of claim 1 wherein the second reagent system comprises at least one chemiluminescent compound and a catalyst.

11. A method for determination of a constituent in a sample which comprises contacting the sample with the device of claim 1 and observing any detectable chemiluminescent response.

12. A method for preparing the test device of claim 1 which comprises incorporating at least one layer with a first reagent system responsive to the presence of an analyte to produce a reaction product and at least one other layer with a second reagent system responsive to the presence of said product to produce luminescence.

* * * * *